US008333709B2

(12) United States Patent
Wang

(10) Patent No.: US 8,333,709 B2
(45) Date of Patent: Dec. 18, 2012

(54) WIRELESS TRANSMISSION VITAL CAPACITY EXAMINING DEVICE

(75) Inventor: Song-hao Wang, Vienna, VA (US)

(73) Assignee: Kun Shan University, Yung-Kang, Tainan Hsien (TW)

( * ) Notice: Subject to any disclaimer, the term of this patent is extended or adjusted under 35 U.S.C. 154(b) by 286 days.

(21) Appl. No.: 12/883,747

(22) Filed: Sep. 16, 2010

(65) Prior Publication Data

US 2012/0071778 A1  Mar. 22, 2012

(51) Int. Cl.
*A61B 5/08* (2006.01)
(52) U.S. Cl. .......................... 600/539; 73/861
(58) Field of Classification Search .................. 600/538, 600/539; 73/1.16, 23.3, 861, 861.351, 861.352, 73/861.353, 861.77, 861.78; 128/204.23, 128/204.26
See application file for complete search history.

(56) References Cited

U.S. PATENT DOCUMENTS

| | | | | |
|---|---|---|---|---|
| 5,277,195 | A | * | 1/1994 | Williams ..................... 600/538 |
| 6,126,613 | A | * | 10/2000 | Edwards et al. .............. 600/539 |
| 6,447,459 | B1 | * | 9/2002 | Larom .......................... 600/538 |
| 2008/0127712 | A1 | * | 6/2008 | Baker ............................. 73/1.16 |
| 2008/0249429 | A1 | * | 10/2008 | Garbe et al. .................. 600/539 |
| 2009/0253994 | A1 | * | 10/2009 | Schuessler et al. .......... 600/538 |
| 2010/0005905 | A1 | * | 1/2010 | Kaspari ..................... 73/861.77 |
| 2011/0152707 | A1 | * | 6/2011 | Jang ............................. 600/539 |

* cited by examiner

*Primary Examiner* — Navin Natnithithadha
*Assistant Examiner* — Etsub Berhanu
(74) *Attorney, Agent, or Firm* — Muncy, Geissler, Olds & Lowe, PLLC

(57) ABSTRACT

A wireless transmission vital capacity examining device includes two induction coils on a stator frame and a rotor frame having a first magnetic area which is mounted to the two induction coils. A rotatable member with rotatable blades has a third connection portion which has a third magnetic area which is magnetically connected to the second magnetic area of rotor frame so as to rotate the rotor frame. The user blows to rotate the blades and the first induction coil outputs a voltage to a processing unit so as to transfer to a value of the vital capacity. The second induction coil provides electric power to the wireless communication unit to transmit the value. The two induction coils are not interfered to each other and the device does not have problem of insufficient voltages.

10 Claims, 4 Drawing Sheets

WIRELESS TRANSMISSION VITAL CAPACITY EXAMINING DEVICE

FIELD OF THE INVENTION

The present invention relates to a wireless transmission vital capacity examining device, and more particularly to one having a stator frame with two independent induction coils to output voltage for examining vital capacity and supplying power. The two induction coils are not interfered to each other and improve the problem of low voltage.

BACKGROUND OF THE INVENTION

A conventional vital capacity examining device generally includes a blowing tube unit which is cooperated with a rotatable member with multiple blades which are driven by the blowing via the blowing tube unit. An electronic circuit detects the revolutions of the blades and determines the vital capacity of the user. However, the device has to be externally and electrically connected with batteries or electric power so as to keep the device to be functioned normally. The transmission of the result of the records is limited by the length of the electric cables that are connected with the device. The conventional vital capacity examining device involves too many parts, consumes electric energy, has high manufacturing cost, is easily broken and affects the preciseness of the result.

SUMMARY OF THE INVENTION

The present invention relates to a wireless transmission vital capacity examining device which improves the shortcomings of the conventional vital capacity examining device. The vital capacity examining device of the present invention comprises a case, a stator frame, a rotor frame, a separation member, a rotatable member, a cover and a processor. The stator frame includes a first induction coil and a second induction coil, and the two induction coils respectively and independently output voltages.

The present invention has the following advantages:

(1) The stator frame has two induction coils which independently output voltages to the device for examining and the two induction coils are not interfered to each other and the device does not have problem of insufficient voltages. There will be no need for external batteries or power source so that the device saves energy, is easily to carry and can be used anytime.

(2) The blades are blown to rotate so that the stator frame and the rotor frame have relative rotation, the first and second induction coils respectively cut magnetic lines to generate voltages. The first induction coil provides electric power to the processing unit so as to detect the change of the voltage according to the volume of the air that blown by the user. The change of voltage is transferred into the vital capacity and displayed on the screen.

(3) The present invention is connected to external storage devices by the output interface thereof so as to store the data of the vital capacity, or is connected to external printing devices to print the result of the data of the vital capacity.

(4) The present invention has a wireless communication unit which transmits the data of the vital capacity to a remote device to be stored, recorded and analyzed. There will be no limit by the distance and is able to be monitored from a remote end so as to immediately deal with the abnormal change of the vital capacity of the user.

(5) The processor of the present invention is modularized and can be directly connected to the case. Once the processor is damaged, the replacement and maintenance are easy and quick.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
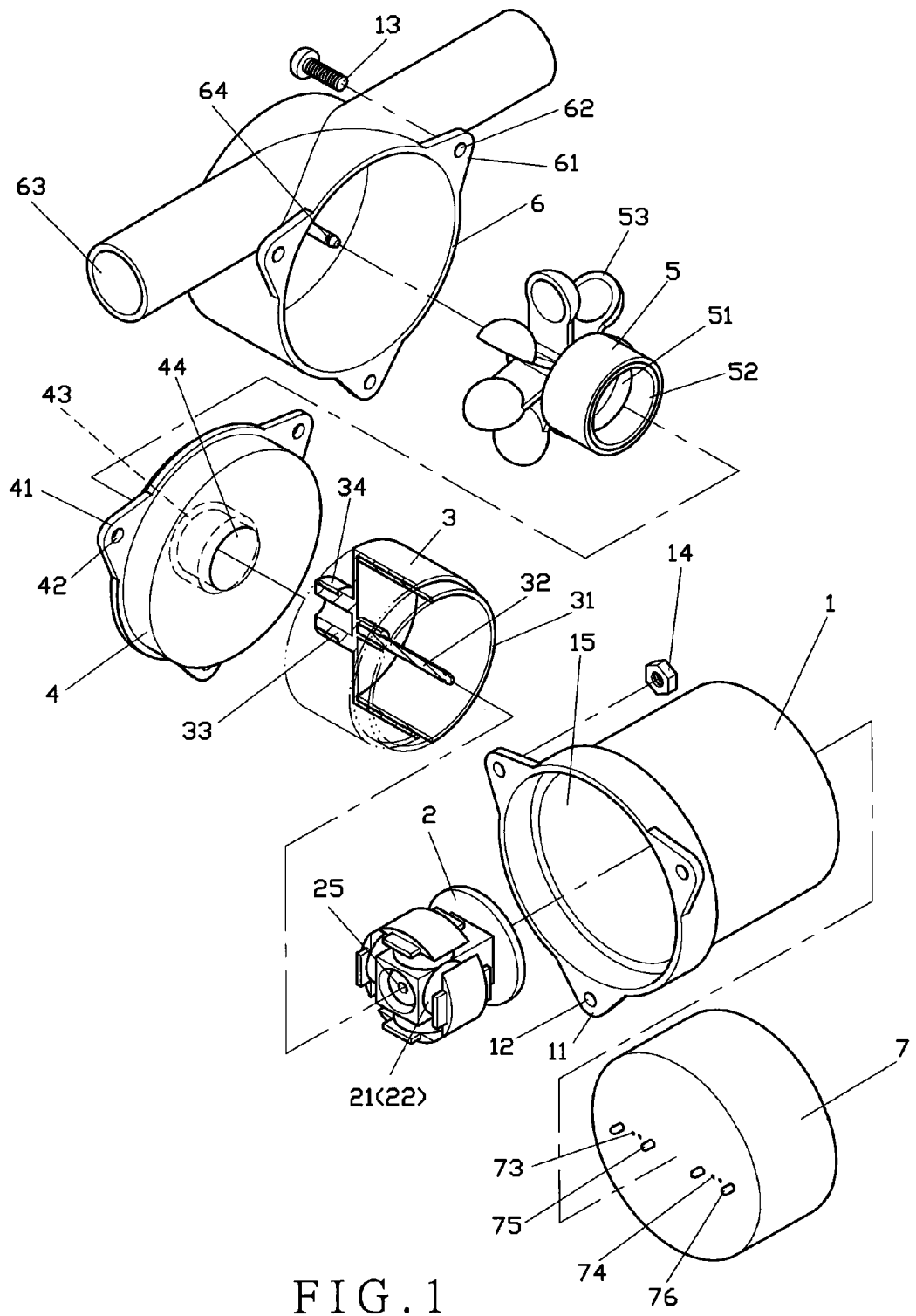
FIG. 1 is an exploded view to show the vital capacity examining device of the present invention.
Figure 2:
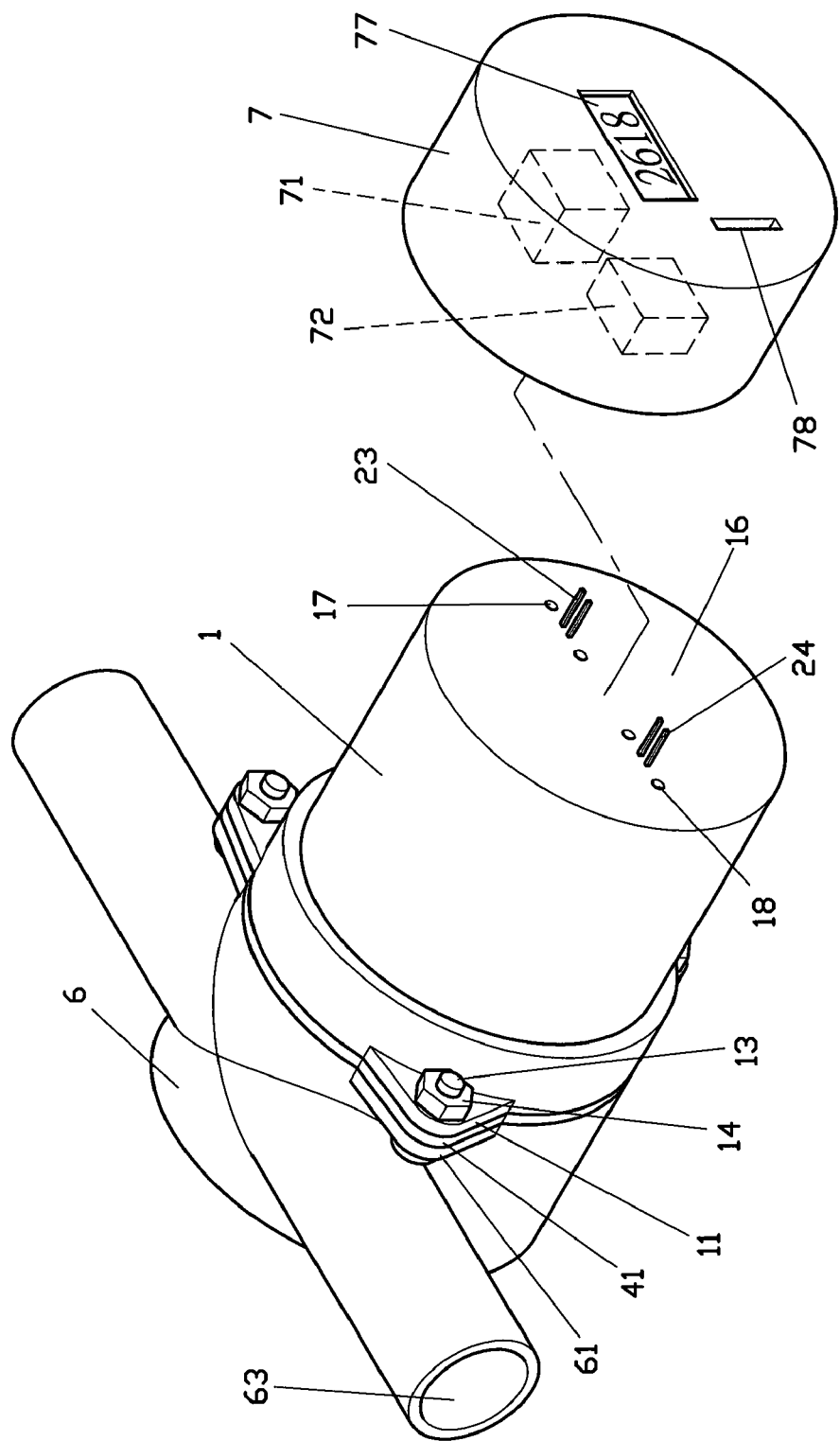
FIG. 2 is an exploded view to show the case and the processor of the vital capacity examining device of the present invention.

Referring to FIGS. 1 and 2, the wireless transmission vital capacity examining device of the present invention comprises a case 1 having first lugs 11 on the outer periphery thereof and each first lug 11 has a first hole 12 for a bolt 13 extending through the first hole 12 and connected with a nut 14. The case 1 has a space 15 defined therein and a connection portion 16 at an outer side thereof. The connection portion 16 has a first positioning hole 17 and a second positioning hole 18.

A stator frame 2 is secured in the space 15 of the case 1 and includes a first induction coil 21 and a second induction coil 22 mounted thereto. The first induction coil 21 includes 2000 turns and is electrically connected to a first output end 23. The second induction coil 22 includes 4000 turns and is electrically connected to a second output end 24. The first and second output ends 23, 24 are terminals which extend through the connection portion 16. The first output end 23 is located corresponding to the first positioning hole 17 and the second output end 24 is located corresponding to the second positioning hole 18. Besides, the stator frame 2 has a first passage 25.

A rotor frame 3 is mounted to the stator frame 2 and has an annular first magnetic area 31 which is a magnet and mounted to the first and second induction coils 21, 22. When the stator frame 2 and rotor frame 3 have relative rotation, the first and second induction coils 21, 22 respectively cut magnetic lines and generate voltages which are respectively output from the first and second output ends 23, 24. The rotor frame 3 has a first shaft 32 which extends through the first passage 25. The rotor frame 3 further has a first connection portion 33 to which an annular second magnetic area 34 is mounted. The second magnetic area 34 is a magnet.

A separation member 4 is fixed to the case 1 and includes second lugs 41 which are located corresponding to the first lugs 11. Each second lug 41 has a second hole 42 for the bolt 13 extending therethrough and connected with the nut 14. The separation member 4 includes a second connection portion 43 which has a reception hole 44. The first connection portion 33 is engaged with the reception hole 44.

A rotatable member 5 is mounted to the separation member 4 and has a third connection portion 51 which is connected with the second connection portion 43. The third connection portion 51 has a third magnetic area 52 which is magnetically connected to the second magnetic area 34 of the rotor frame 3 while the second connection portion 43 is located therebetween. The rotatable member 5 has multiple blades 53 rotatably connected thereto and a second passage 54 is defined in the rotatable member 5 as shown in FIG. 3.

A cover 6 is fixed to the separation member 4 and has third lugs 61 which are located corresponding to the second lugs 41. Each of the third lugs 61 has a third hole 62 and multiple bolts 13 extend through the first, second and third lugs 11, 41, 61 and are connected with nuts 14 so as to connect the case 1, the separation member 4 and the cover 6 together. The cover 6 further includes a blowing passage 63 which is located corresponding to the trace of any of the blades 53 of the rotatable member 5. The cover 6 has a second shaft 64 which extends through the second passage 54.

A processor 7 is connected to the connection portion 16 of the case 1 and has a processing unit 71 and a wireless communication unit 72 which is electrically connected to the processing unit 71. The processing unit 71 is electrically connected to a first input end 73 and the first output end 23 so as to receive the voltage from the first induction coil 21. The first input end 73 is a hole. The wireless communication unit 72 is electrically connected with a second input end 74. The second input end 74 is a hole in which the second output end 24 is inserted so as to receive the voltage from the second induction coil 22. The processor 7 has a first rod 75 close to the first input end 73 and a second rod 76 close to the second input end 74. The first rod 75 is inserted into the first positioning hole 17 and the second rod 76 is inserted into the second positioning hole 18. The processor 7 further has a screen 77 and an output interface 78. The output interface 78 is a USB slot. The screen 77 and the output interface 78 are respectively and electrically connected to the processing unit 71.

Figure 3:
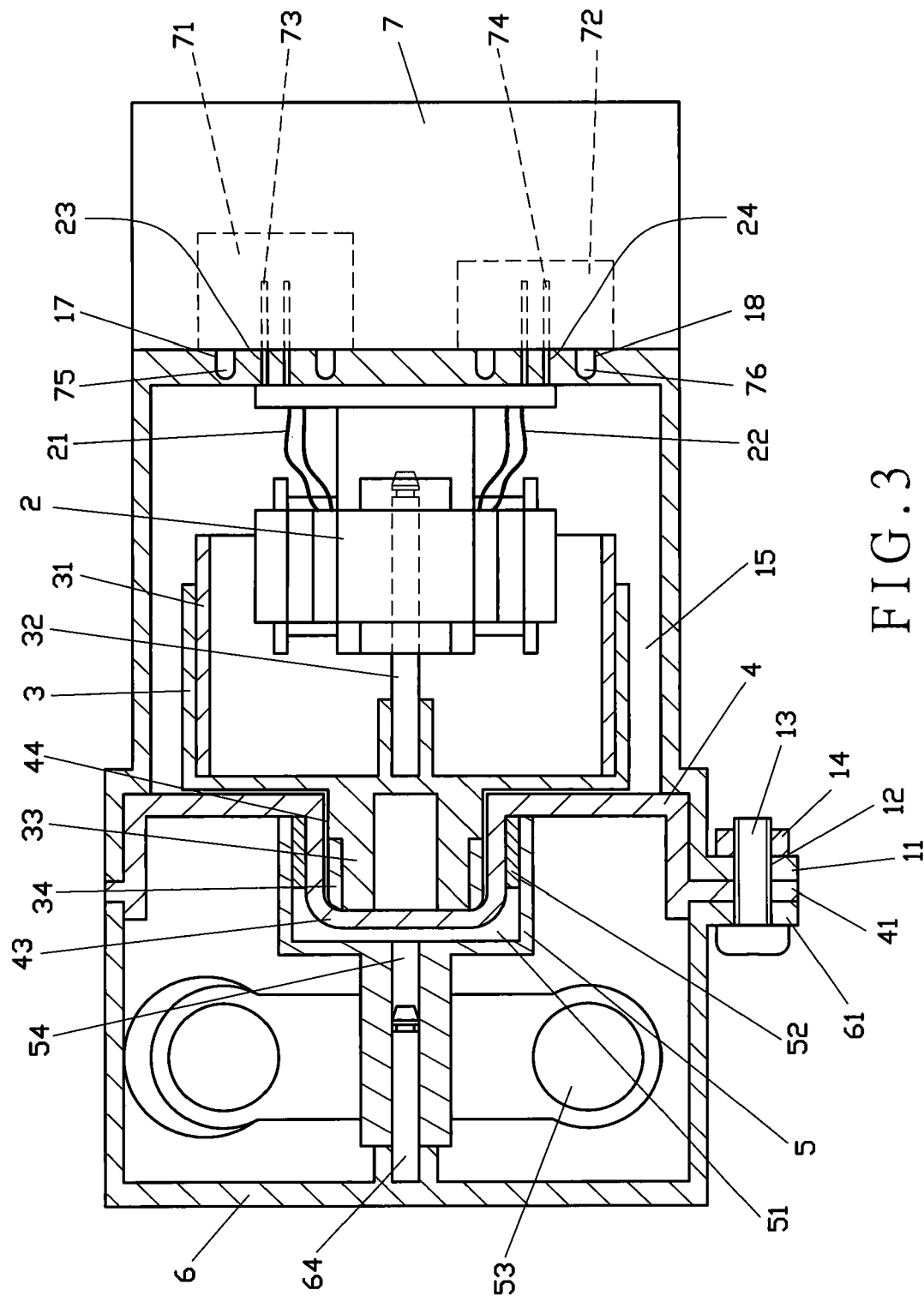
FIG. 3 is a cross-sectional view of the vital capacity examining device of the present invention.
Figure 4:
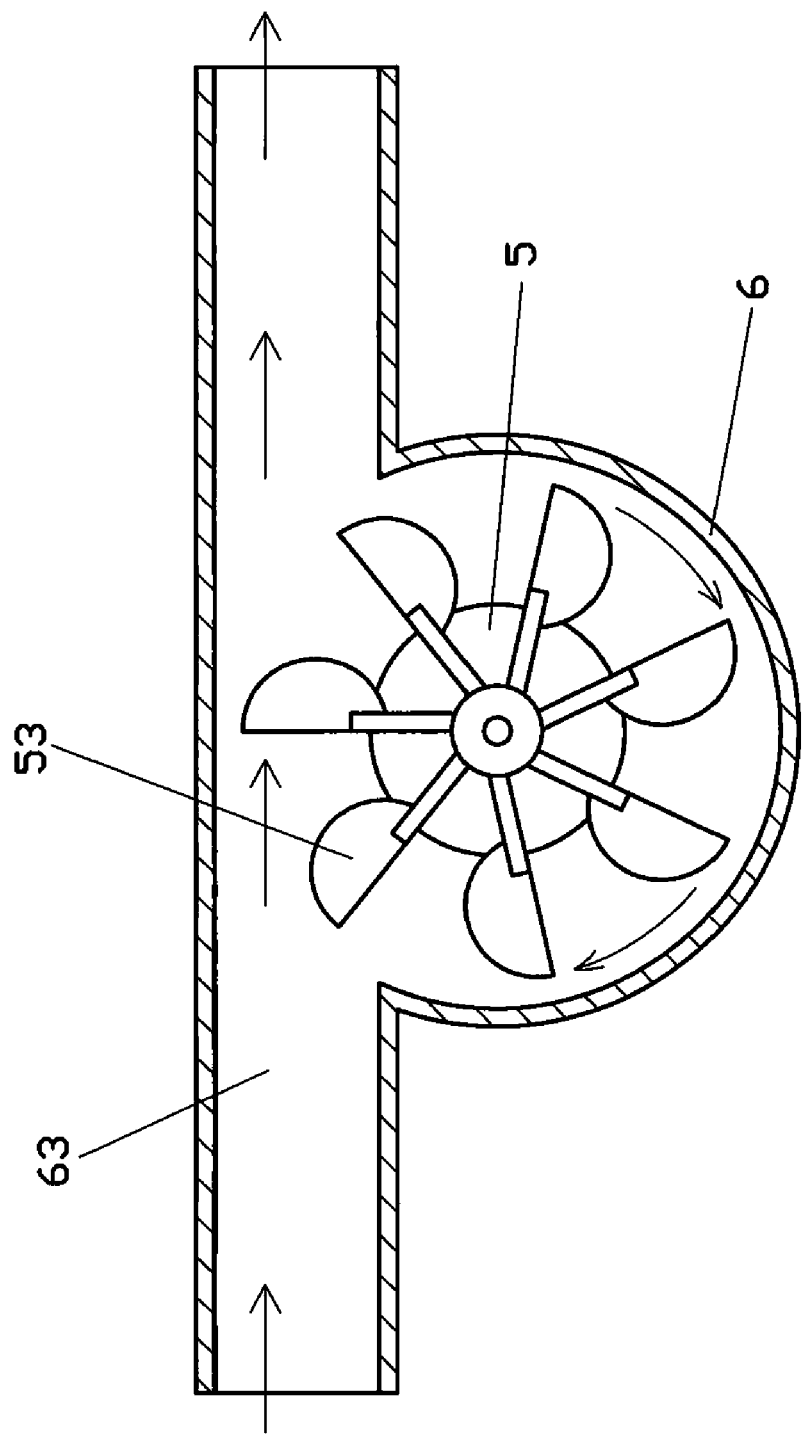
FIG. 4 shows that the blades of the rotatable member are blown to rotate.

As shown in FIGS. 3 and 4, when a user blows to the blowing passage 63 of the cover 6, the air pushes the blades 53 to rotate. The third magnetic area 52 of the third connection portion 51 of the rotatable member 5 is magnetically connected to the second magnetic area 34 of the rotor frame 3, while the second connection portion 43 is located there between. The rotor frame 3 is rotated by the first connection portion 33 and the first magnetic area 31 is rotated relative to the first and second induction coils 21, 22, such that the first and second induction coils 21, 22 respectively cut the magnetic lines to generate voltages. The voltages are output via the first and second output ends 23, 24, wherein the voltage from the first output end 23 is transferred to the processing unit 71 via the first input end 73. The processing unit 71 detects the change of the voltages according to the volume of the blowing air so as to transfer the change into data of the vital capacity. The data is recorded and displayed on the screen 77. The processor 7 has the output interface 78 which is electrically connected to the processing unit 71 so as to store the data of the examined vital capacity or the data vital capacity can be printed out by printing devices. The voltage from the second output end 24 can be transmitted to the wireless communication unit 72 via the second input end 74 so as to power the wireless communication unit 72. The data of the vital capacity detected by the processing unit 71 can be transmitted to a remote device for storage, recorded, analyzed and monitored by the wireless communication unit 72. Once the value of the vital capacity of the user is abnormal, the situations can be quickly handled and processed. In addition, the moisture during blowing is separated from entering the space 15 by the separation member 4, so that the parts in the space 15 can be protected from shortage or damaged.

While we have shown and described the embodiment in accordance with the present invention, it should be clear to those skilled in the art that further embodiments may be made without departing from the scope of the present invention.

What is claimed is:

1. A wireless transmission vital capacity examining device, comprising:
    a case having a space defined therein and a connection portion;
    a stator frame secured in the space of the case and having a first induction coil and a second induction coil, the first induction coil electrically connected to a first output end and the second induction coil electrically connected to a second output end;
    a rotor frame mounted to the stator frame and having a first magnetic area which is located corresponding to the first and second induction coils, the rotor frame having a first connection portion to which a second magnetic area is formed;
    a separation member fixed to the case and including a second connection portion which has a reception hole, the first connection portion engaged with the reception hole;
    a rotatable member mounted to the separation member and having a third connection portion, the third connection portion connected with the second connection portion, the third connection portion having a third magnetic area which is magnetically connected to the second magnetic area, the rotatable member having multiple blades rotatably connected thereto;
    a cover fixed to the separation member and having a blowing passage which is located corresponding to the blades of the rotatable member, and
    a processor connected to the connection portion of the case and having a processing unit and a wireless communication unit, the processing unit electrically connected to a first input end and the first output end, the wireless communication unit electrically connected with a second input end and the second output end, the processor having a screen which is electrically connected to the processing unit.

2. The device as claimed in claim 1, wherein the case has first lugs and each of the first lugs has a first hole, the separation member has second lugs which are located corresponding to the first lugs, each of the second lugs has a second hole, the cover has third lugs which are located corresponding to the second lugs, each of the third lugs has a third hole, multiple bolts extend through the first, second and third lugs and are connected with nuts to connect the case, the separation member and the cover together.

3. The device as claimed in claim 1, wherein the first induction coil includes 2000 turns and the second induction coil includes 4000 turns.

4. The device as claimed in claim 1, wherein the first and second output ends are terminals which extend through the connection portion, the first input end is a hole in which the first output end is inserted, the second input end is a hole in which the second output end is inserted.

5. The device as claimed in claim 1, wherein the connection portion includes a first positioning hole and a second positioning hole, the processor has a first rod and a second rod, the first rod is inserted into the first positioning hole and the second rod is inserted into the second positioning hole.

6. The device as claimed in claim 1, wherein the stator frame has a first passage and the rotor frame has a first shaft which extends through the first passage.

7. The device as claimed in claim 1, wherein the rotatable member has a second passage and the cover has a second shaft which extends through the second passage.

8. The device as claimed in claim 1, wherein the processor has an output interface which is electrically connected to the processing unit.

9. The device as claimed in claim 8, wherein the output interface is a USB (Universal Serial Bus) slot.

10. The device as claimed in claim 1, wherein the first, second and third magnetic areas are magnets.

* * * * *